United States Patent [19]
Van Tassel

[11] Patent Number: 5,776,174
[45] Date of Patent: Jul. 7, 1998

[54] STABILIZATION OF VASCULAR LESIONS BY ULTRAVIOLET RADIATION

[75] Inventor: Robert A. Van Tassel, Excelsior, Minn.

[73] Assignee: Illumenex Corporation, Plymouth, Minn.

[21] Appl. No.: 382,095

[22] Filed: Jan. 30, 1995

[51] Int. Cl.$^6$ ............................................. A61N 5/06
[52] U.S. Cl. ................................... 607/89; 606/3; 606/15
[58] Field of Search ........................... 604/20, 21, 50–53; 607/88–90, 92–94; 606/3, 7, 2, 10, 13–18

[56] References Cited

U.S. PATENT DOCUMENTS

| | | | |
|---|---|---|---|
| 4,512,762 | 4/1985 | Spears | 604/21 |
| 4,850,351 | 7/1989 | Herman et al. | 604/21 |
| 5,005,180 | 4/1991 | Edelman et al. | 604/21 |
| 5,053,033 | 10/1991 | Clarke | 606/3 |
| 5,188,632 | 2/1993 | Goldenberg | 606/7 |
| 5,370,608 | 12/1994 | Sahota et al. | 604/20 |
| 5,417,653 | 5/1995 | Sahota et al. | 604/20 |
| 5,453,448 | 9/1995 | Narciso, Jr. | 606/2 |
| 5,514,707 | 5/1996 | Deckelbaum et al. | 514/455 |

*Primary Examiner*—Lee S. Cohen
*Assistant Examiner*—Bryan K. Yarnell
*Attorney, Agent, or Firm*—Thomas J. Engellenner; Jane E. Remillard; Lahive & Cockfield, LLP

[57] ABSTRACT

Ultraviolet radiation can be used to treat vascular diseases. In particular, for unstable lesions where angioplasty may not be warranted, cytotoxic, nonablative ultraviolet radiation, preferably at a wavelength in the range of about 240 to about 280 nanometers, can be used to disable the intima and reduce spasms associated with partially occluded blood vessels.

6 Claims, 3 Drawing Sheets

STABILIZATION OF VASCULAR LESIONS BY ULTRAVIOLET RADIATION

BACKGROUND OF THE INVENTION

The present invention relates to methods for treating unstable atherosclerotic lesions using cytotoxic, nonablative ultraviolet radiation.

Atherosclerosis is a disease which causes thickening and hardening of the arteries. It is characterized by lesions of raised fibrous plaque formed within the arterial lumen. Atherosclerotic plaque is commonly treated by means of angioplasty through the use of a balloon catheter. Balloon angioplasty involves passing a small, balloon-tipped catheter percutaneously into an artery and up to the region of obstruction. The balloon is then inflated to dilate the area of obstruction. Other devices, such as atherectomy instruments, which remove obstructions by peeling or shaving plaque from the artery wall, can also be utilized in the treatment of atherosclerosis.

More recently, laser systems have been proposed for performing angioplasty. In laser angioplasty, a catheter carrying a fiber optic waveguide is passed through a blood vessel, positioned near an obstruction, and then activated to decompose the plaque with laser radiation.

Unfortunately, restenosis, or closure of the blood vessel following angioplasty, is a common-occurrence following all types of such surgery. Angioplasty and atherectomy procedures to open a stenosis or closed blood vessel are highly invasive procedures which induces injury to the arterial wall. Such operations often cause medial smooth muscle cells of the arterial wall to proliferate in response to this injury. This proliferation is believed to contribute, at least in part, to restenosis.

It is known from U.S. Pat. No. 5,053,033 that such restenosis following angioplasty can be inhibited by irradiating the angioplasty site with ultraviolet radiation to kill a portion of the smooth muscle cells. In particular, U.S. Pat. No. 5,053,033 discloses that ultraviolet radiation, preferably at a wavelength ranging from about 240 nanometers to about 280 nanometers can have cytotoxic effects and kill a large percentage of the smooth muscle cells after angioplasty but before proliferation occurs.

While angioplasty followed by ultraviolet radiation to inhibit restenosis may be one method to treat occluded blood vessels, many atherosclerotic lesions do not warrant invasive treatment by angioplasty or atherectomy. For example, many lesions are characterized by a raised fibrous plaque which is not yet substantially obstructing a blood vessel. Such a condition may not necessitate angioplasty to physically open the obstruction, but the lesion still has the potential to thicken further and eventually cause a more severe obstruction, vasospasms, or the cup of the fibrous plaque may rupture, leading to thrombosis of the vessel. These lesions may be associated with reduced medial smooth muscle cell layers of the blood vessel wall and certain biochemical changes in the intima or inner surface of the blood vessel which cause platelet attraction and blood coagulation over time.

There exists a need for a method of stabilizing such lesions or preventing further plaque development without risking injury to the arterial wall by invasive angioplasty. Accordingly, it is an object of the present invention to provide a method of stabilizing atherosclerotic lesions without physically altering the lesion site.

SUMMARY OF THE INVENTION

Atherosclerotic lesions can be treated and stabilized without mechanically assaulting or otherwise physically reshaping the lesion by irradiating the lesion with cytotoxic, nonablative ultraviolet (UV) radiation. Such radiation, preferably ranging from about 240 nanometers to about 280 nanometers, kills or inactivates smooth muscle cells of the blood vessel wall, thereby reducing the potential for vasospasms. The smooth muscle cells of the plaque are also inactivated and prevented from migrating by this treatment. The UV radiation is preferably delivered via an optical fiber or other waveguide incorporated, for example, into a percutaneous catheter.

Various UV radiation sources can be use in accordance with the present invention to deliver lesion stabilizing therapy without physically reshaping or altering the lesion, including both laser and non-coherent radiation sources. The terms "without physically reshaping" and "without physically altering" are defined herein as encompassing procedures which treat vascular lesions without physically removing atherosclerotic plaque by, for example, using a plaque shaving device or ablative radiation, or by mechanically opening the lumen, or by applying pressure to dilate the area of obstruction using a balloon catheter or the like. Either pulsed or continuous wave ("CW") lasers can be used in the present invention, and the lasant medium can be gaseous, liquid or solid state. One preferred laser source is a pulsed excimer laser, such as a KrF laser. Alternatively, rare earth-doped solid state lasers, ruby lasers and Nd:YAG lasers can be operated in conjunction with frequency modification means to produce an output beam at the appropriate UV wavelength. In another alternative, a UV flash lamp can be employed.

The UV radiation source preferably produces an output beam having a wavelength less than about 280 nanometers. The therapeutic UV radiation useful in the present invention will typically range from about 280 nanometers down to about 240 nanometers (due to the limited transmission efficiency of glass fibers at lower wavelengths). In one preferred embodiment, a laser system is disclosed which operates at about 266 nanometers to maximize the cytotoxic effect of the radiation. Other useful UV radiation sources include, for example, Argon ion lasers emitting UV light at about 257 or 275 nanometers and KrF excimer lasers emitting light at about 248 nanometers.

The invention can be practiced with a low energy radiation source. The term "low energy" is used herein to describe both laser and non-coherent radiation systems having an energy output of less than about 5 J/cm$^2$ per pulse for pulsed lasers, or a total dose of less than about 1000 J/cm$^2$, more preferably less than 100 J/cm$^2$, for continuous wave lasers or non-coherent radiation sources.

In one illustrated embodiment of the invention, at least one optical fiber for transmission of UV radiation is incorporated into a conventional percutaneous catheter and operated to deliver therapeutical UV radiation to the lesion site. In this embodiment, the therapeutic radiation can be provided by a single laser or a plurality of lasers operating in tandem to deliver cytotoxic, nonablative laser radiation.

In another aspect of the invention, novel UV radiation sources are disclosed herein. In one illustrated embodiment, a laser having an output beam wavelength of about 1064 nanometers, such as a common Nd:YAG laser, can be used in conjunction with two doubling crystals to yield a radiation output of about 266 nanometers. Similarly, a Nd:YLF laser operating at about 1047 nanometers can be used in conjunction with two frequency doubling crystals.

Novel catheter systems are also disclosed herein. Such catheter systems are useful in the performance of laser angioplasty and are preferably equipped with at least one optical waveguide for delivery of the UV radiation therapy, which can be, for example, an optical fiber having about a 200 micron diameter core. The catheter tip can also contain focusing optics or diffusive elements for use in directing the radiation emitted from the catheter within an artery.

The invention will next be described in connection with certain illustrated embodiments. However, it should be clear that various changes and modifications can be made by those skilled in the art without departing from the spirit or scope of the invention.

DETAILED DESCRIPTION

Figure 1:
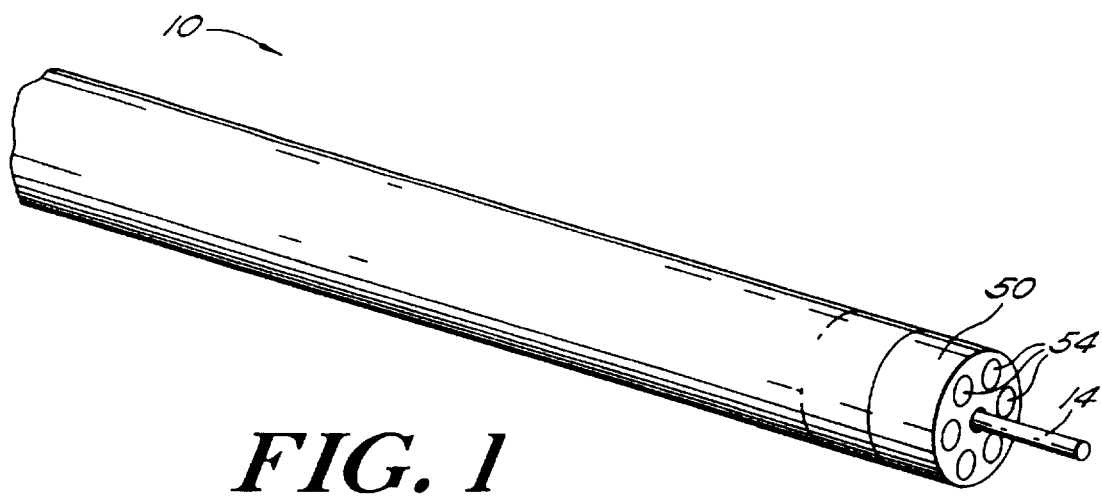
FIG. 1 is a schematic perspective view of a laser therapy catheter for stabilizing atherosclerotic lesions without physically reshaping the lesion site.
Figure 2:
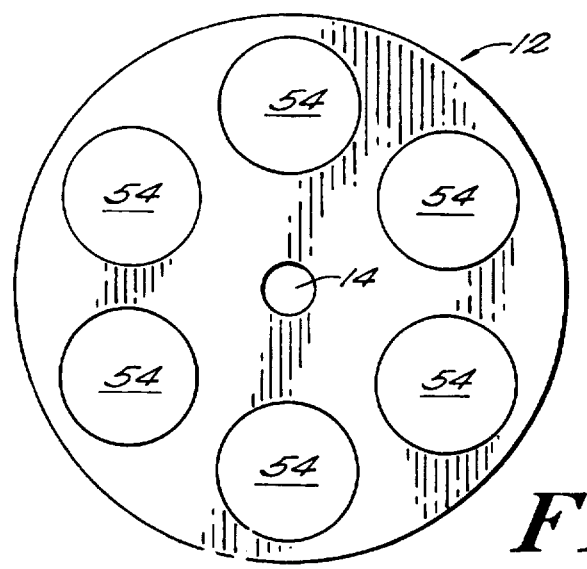
FIG. 2 is a view of the distal end of the catheter of FIG. 1.

In FIG. 1, a laser therapy catheter 10 is shown, including a guide wire 14. Also disposed within the catheter are a plurality of optical fibers 54 for delivery of ultraviolet radiation. The catheter can also include a radio-opaque tip 50. In FIG. 2, the distal end 12 of the catheter of FIG. 1 is shown in more detail, including an exemplary disposition of six optical fibers 54 about a central guide wire 14. Alternatively, the distal end of the catheter can include an optically diffusive tip, as known in the art, which serves to diffuse the UV radiation from one or more optical fibers into a circumferential or partially circumferential pattern.

Figure 3A:
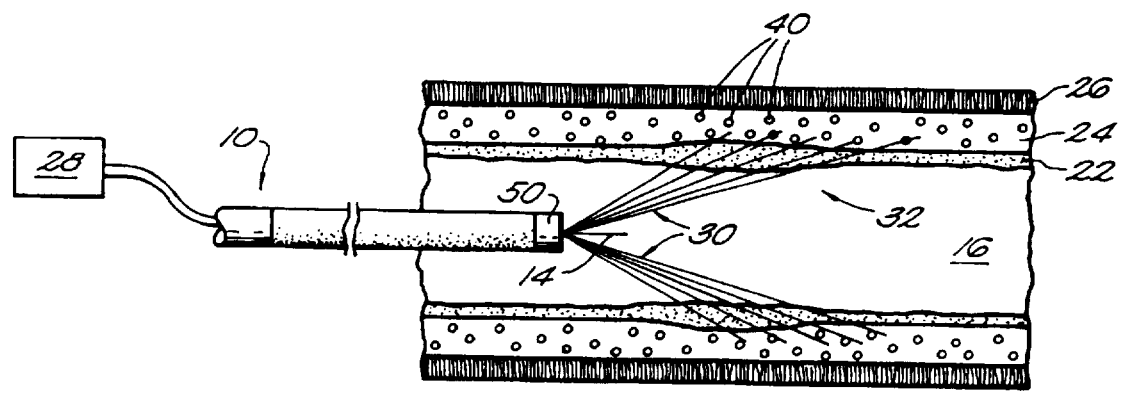
FIGS. 3A–3B are schematic cross-sectional illustrations of a system incorporating the catheter of FIG. 1.
Figure 3B:
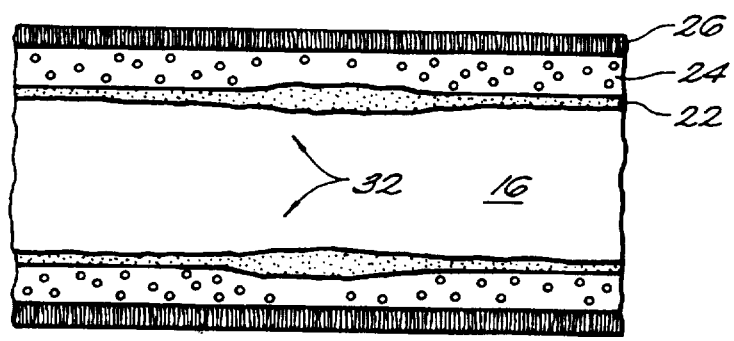

The use of the catheter system 10 is schematically illustrated in FIGS. 3A–3B. In use, the guide wire 14 is first introduced into the obstructed blood vessel and used to guide the catheter 10 into position adjacent to the plaque or lesion (e.g., under radiographic control). As shown in FIG. 3A, the distal tip of the catheter is then positioned to deliver UV radiation therapy to the lesion 32. A therapeutical laser 28 can then be activated to deliver UV radiation 30 which will kill a major portion of the smooth muscle cells 40 within the media 24 of the blood vessel wall without physically reshaping the lesion and without damaging either the inner endothelium layer 22 or the outer adventitia 26 of the blood vessel. The energy of the UV radiation can be about 5 J/cm$^2$ per pulse or less for pulsed lasers, or a total dose of about 1000 J/cm$^2$ or less. The power density of the radiation is preferably less than 5 watts per square centimeter, more preferably less than 2 watts per square centimeter.

As shown in FIG. 3B, by killing or inactivating a major portion of the smooth muscle cells in the vicinity of the lesion, the end result of the treatment is substantially fewer, if any, smooth muscle cells remaining in the lesion site to proliferate or migrate and cause lesion instability. Thus, the capability of the blood vessel wall to constrict or produce vasospasms is substantially limited or completely removed.

Figure 4:
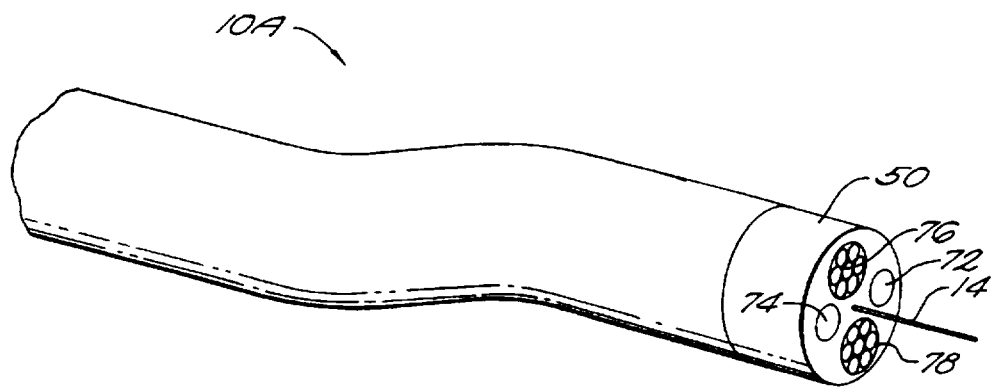
FIG. 4 is a schematic perspective view of an alternative catheter for delivering nonablative, cytotoxic UV radiation to the site of an unstable lesion.
Figure 5:
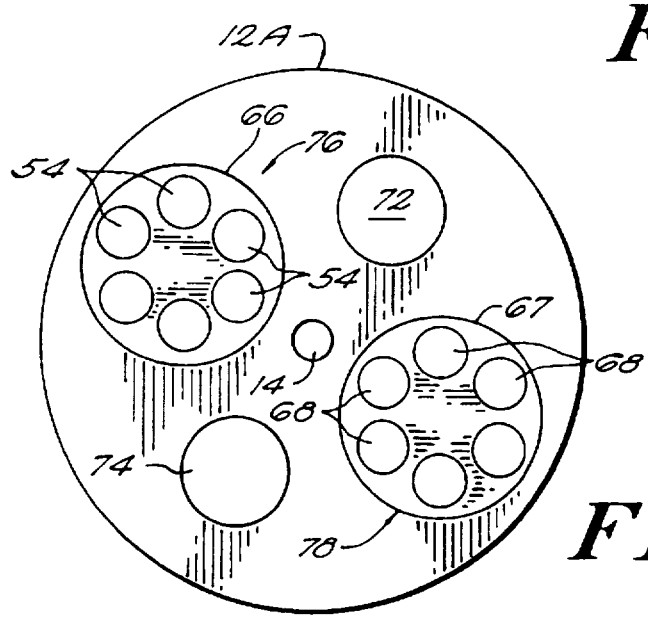
FIG. 5 is a view of the distal end of the catheter of FIG. 4.

In FIGS. 4 and 5, an alternative catheter configuration 10A for delivering therapeutic, nonablative UV radiation to the site of an unstable atherosclerotic lesion is shown, including a guide wire 14 and two laser radiation delivery systems 76 and 78. The laser delivery systems 76 provide therapeutic UV radiation to inactivate smooth muscle cells in the vicinity of the lesion, thereby stabilizing the lesion. Like the system of FIG. 1, the catheter of FIG. 4 can also include a radio-opaque tip 50 to aid in positioning the catheter within a blood vessel under radiographic control. The second laser delivery system 78 can provide illumination and viewing fibers or a second source of therapeutic (or even ablative) radiation (e.g., at a different wavelength or energy fluence).

As shown in more detail in FIG. 5, the distal end of 12A of the catheter can include two therapeutic UV radiation delivery systems 76 and 78. Multiple optical fibers 54 for UV radiation therapy are encased in sleeve 66 which is positioned on one side of the guide wire 14 to provide the UV therapy system. A similar sleeve 67 encasing the second set of optical fibers 68 forms the second radiation therapy subsystem 78 disposed on the opposite side of the guide wire 14. The catheter can further include a flushing port 72 for the introduction of saline at the site and/or a suction port 74 for clearing the site of fluids during laser operations.

The catheter system 10A operates essentially in the same manner as system 10 described in FIGS. 3A and 3B.

Figure 6:
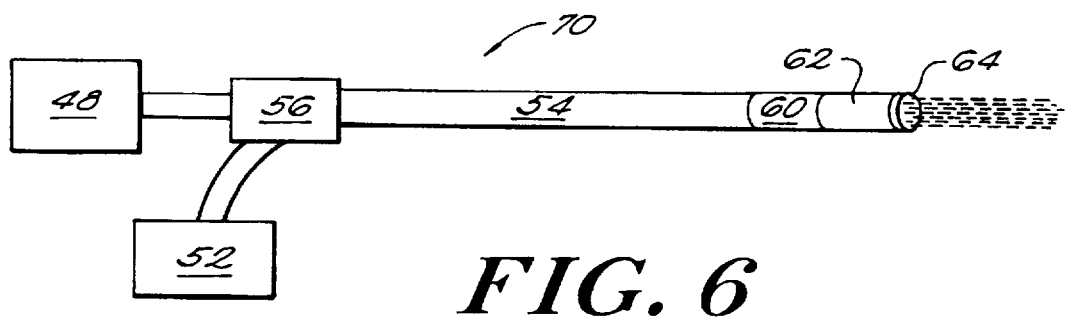
FIG. 6 is a schematic illustration of a laser device useful in the present invention.

As noted above, the therapeutic UV radiation can be provided by a variety of sources, including non-coherent UV light sources and excimer laser sources (e.g., an Argon ion laser operating at about 275 nanometers or a KrF excimer laser operating at 248 nanometers). In FIG. 6, an alternative laser device 70 is shown which can be used in the present invention to provide the therapeutic UV radiation. In the system 70, an output beam from a laser source 48, such as Nd:YAG laser with an output radiation having a wavelength of about 1064 nanometers is introduced via coupler 56 into an optical fiber 54 which is preferably a rare earth-doped silica fiber (e.g. a Neodymium-doped optical fiber). As the radiation from laser source 48 is introduced into the optical fiber 54, the fiber is also optically pumped by an optical pump source 52 (e.g., a laser diode having an output radiation wavelength of about 808 nanometers, likewise coupled to the fiber 54 by coupler 56). The doped optical fiber thus acts a laser amplifier.

At the distal end of fiber 54, the system is terminated in two frequency-multiplying crystals 60 and 62. The first crystal 60 is a frequency-doubling optical element, such as a potassium dihydrogen phosphate (KDP) crystal, and the second crystal 62 is also a frequency-doubling optical element, such as a barium boron oxide (BBO) crystal. Focusing optics 64, such as a grated refractive index ("GRIN") lens, can be included at the output end of the optical fiber 54. With the system as described, therapeutic laser radiation of a wavelength of about 266 nanometers is produced.

The therapeutic radiation useful in stabilizing lesions in accordance with the present invention is preferably delivered at an energy level below the threshold for ablation. This ablation threshold will vary depending on the wavelength of the radiation. Table 1, below, provides guidance with reference to a number of commonly used UV emission bands. As can be seen from Table 1, the therapeutic dose of radiation for stabilizing vascular lesions using a pulsed radiation source will typically employ radiation at less than about 5 J/cm$^2$ per pulse, preferably less than 2 J/cm$^2$ per pulse and, in many applications, less than 1 J/cm$^2$ per pulse. The present invention is thus intended to operate well below the ablation threshold.

TABLE 1

| WAVELENGTH | ENERGY FLUENCE |
|---|---|
| 350 nm | 4.2 J/cm$^2$ |
| 308 nm | 1.4 J/cm$^2$ |
| 266 nm | 1.0 J/cm$^2$ |
| 248 nm | .35 J/cm$^2$ |
| 222 nm | .22 J/cm$^2$ |
| 193 nm | .13 J/cm$^2$ |

Whether radiation is pulsed or continuous wave, it is important to minimize the total dose delivered to the target vascular region. For a typical treatment protocol, the total dose will usually be less than 1000 J/cm$^2$, preferably less than 100 J/cm$^2$, and more preferably less than 20 J/cm$^2$, regardless of the nature of the radiation (i.e., pulsed or continuous wave).

The present invention can also be practiced in conjunction with the systemic administration of therapeutic agents that enhance the effects of site irradiation. For example, a chromophore, such as psoralen, can be administered prior to irradiation of the lesion site. The psoralen will be absorbed by the smooth muscle cells, thus rendering them more susceptible to the UV light.

Those skilled in the art will be able to recognize, or be able to ascertain using no more than routine experimentation, numerous equivalents to the specific compositions and procedures described herein. Such equivalents are considered to be within the scope of this invention and are covered by the following claims.

What we claim is:

1. A method of treating an unstable atherosclerotic lesion comprising:

disposing an optical waveguide means inside a blood vessel;

locating the waveguide means adjacent to an atherosclerotic lesion site within the vessel; and irradiating the lesion site with non-ablative, cytotoxic UV radiation having a wavelength ranging from about 240–280 nanometers via said optical waveguide means to inactivate smooth muscle cells in the vicinity of the lesion site without the use of either angioplasty or a photoactivatable psoralen.

2. The method of claim 1 wherein the step of irradiating the lesion site further serves to reduce the migration of smooth muscle cells.

3. The method of claim 1 wherein the UV radiation is low power UV radiation.

4. The method of claim 1 wherein the UV radiation has power density of about 5 watts per square centimeter or less.

5. The method of claim 1 wherein the total dose of UV radiation administered to the lesion site is about 1000 Joules per square centimeter or less.

6. The method of claim 1 wherein the UV radiation is pulsed UV radiation having an energy of about 5 millijoules per pulse or less.

* * * * *